United States Patent [19]
Klaveness et al.

[11] Patent Number: 5,817,289
[45] Date of Patent: Oct. 6, 1998

[54] NON-CLUSTER TYPE BISMUTH COMPOUNDS

[75] Inventors: Jo Klaveness, Oslo; Arne Berg, Sandvika, both of Norway; Torsten Almén, Falsterbo, Sweden; Klaes Golman, Rungsted Kyst, Denmark; Michael Droege, Livermore; S. B. Yu, Campbell, both of Calif.

[73] Assignee: Nycomed Imaging AS, Norway

[21] Appl. No.: 486,225

[22] Filed: Jun. 7, 1995

[30] Foreign Application Priority Data

Jan. 26, 1995 [GB] United Kingdom .................. 9501560

[51] Int. Cl.[6] ........................... A61K 51/00; A61M 36/14
[52] U.S. Cl. ...................... 424/1.11; 424/1.65; 424/9.1; 424/9.3; 424/9.4
[58] Field of Search .................... 424/1.11, 1.37, 424/1.65, 1.81, 1.85, 9.1, 9.3, 9.36, 9.4, 9.42, 9.44, 9.45, 9.451, 9.5; 534/10–16; 556/1, 28, 64, 70–71, 76

[56] References Cited

U.S. PATENT DOCUMENTS

| | | |
|---|---|---|
| 3,239,411 | 3/1966 | Leebrick et al. . |
| 3,247,050 | 4/1966 | Leebrick et al. . |
| 3,466,366 | 9/1969 | Leebrick . |
| 3,753,990 | 8/1973 | Downing . |
| 3,824,307 | 7/1974 | Curry . |
| 4,153,685 | 5/1979 | Serfontein . |
| 4,588,589 | 5/1986 | Sheth et al. . |
| 4,647,447 | 3/1987 | Gries et al. . |
| 4,652,519 | 3/1987 | Warschawsky et al. . |
| 4,687,659 | 8/1987 | Quay . |
| 4,826,673 | 5/1989 | Dean et al. . |
| 5,008,256 | 4/1991 | Clitherow . |
| 5,013,560 | 5/1991 | Stentz et al. . |
| 5,229,418 | 7/1993 | Collington et al. . |
| 5,273,984 | 12/1993 | Clitherow . |
| 5,482,699 | 1/1996 | Almen et al. ........................... 424/9.42 |
| 5,482,700 | 1/1996 | Deutsch et al. ........................ 424/9.42 |

FOREIGN PATENT DOCUMENTS

| | | |
|---|---|---|
| 809388 | 5/1974 | Belgium . |
| 0 0217 577 A2 | 9/1986 | European Pat. Off. . |
| 0 230 893 A2 | 1/1987 | European Pat. Off. . |
| 0 445 743 A2 | 9/1991 | European Pat. Off. . |
| 0 480 691 A2 | 4/1992 | European Pat. Off. . |
| 0 0533 281 A1 | 9/1992 | European Pat. Off. . |
| 0 716 091 A1 | 8/1994 | European Pat. Off. . |
| 2216725 | 10/1973 | Germany . |
| 63-225391 | 9/1988 | Japan . |
| 81/7456 | 4/1983 | South Africa . |
| 1003685 | 9/1965 | United Kingdom . |
| 1341331 | 12/1973 | United Kingdom . |
| 2 248 185 | 1/1992 | United Kingdom . |
| 2 262 036 | 6/1993 | United Kingdom . |
| WO 89/00557 | 1/1989 | WIPO . |
| WO 89/03219 | 4/1989 | WIPO . |
| WO 91/03241 | 3/1991 | WIPO . |
| WO 92/01457 | 2/1992 | WIPO . |
| WO 92/17215 | 10/1992 | WIPO . |
| WO 93/02713 | 2/1993 | WIPO . |
| WO 95/06053 | 3/1995 | WIPO . |
| WO 96/16677 | 6/1996 | WIPO . |
| WO 96/16678 | 6/1996 | WIPO . |

OTHER PUBLICATIONS

Suzuki et al., "Ultrasonic Reaction of Triarylbismuthines and Trarylstibines with Iodosylbenzene.", Tetrahedron Letters, vol. 35, No. 44, pp. 8197–8200, 1994.

Sharutin et al., "Reactions of Vanadocene and Cobaltocene with Dichlorotriphenyl–Antimony and with Dichlorotriphenylbismuth", Blagoveshchensk Tech. Inst. vol. 61, No. 6–1357–1359, Jun. 1991.

A. Ashana, "Reactions of triphenyl antimony, bismuth and their dibromides with pentacholorophenol and pentachlorothiophenol", Chemical Abstracts, Organometallics vol. 121, 1994, 157769.

*Primary Examiner*—Gary E. Hollinden
*Assistant Examiner*—Dameron Jones
*Attorney, Agent, or Firm*—Fish & Richardson PC

[57] ABSTRACT

The use in diagnostic imaging, in particular X-ray, MRI, ultrasound and scintigraphy, of contrast agents comprising bismuth clusters and/or organic bismuth compounds, and contrast media containing such bismuth compounds. The bismuth compounds are also useful in therapy, in particular as antimicrobial agents and antiulcer agents. Novel bismuth compounds are also disclosed.

14 Claims, No Drawings

NON-CLUSTER TYPE BISMUTH COMPOUNDS

The present invention relates to the use in diagnostic imaging, in particular X-ray, MRI, ultrasound and scintigraphy, of contrast agents comprising organic bismuth compounds, and to contrast media containing such bismuth compounds. Another aspect of the present invention is the use of the bismuth compounds in therapy, in particular as antimicrobial agents and antiulcer agents.

All diagnostic imaging is based on the achievement of different signal levels from different structures within the body. Thus in X-ray imaging, for example, for a given body structure to be visible in the image the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedure, i.e. increased contrast can lead to increased spatial resolution.

The diagnostic quality of images is strongly dependent on the inherent noise level in the imaging procedure—the ratio of the contrast level to the noise level can thus be seen to represent an effective diagnostic quality factor for diagnostic images.

Achieving improvement in such a diagnostic quality factor has long been and still remains an important goal. In techniques such as X-ray and ultrasound, one approach to improve the diagnostic quality factor has been to introduce contrast enhancing materials, contrast agents, into the body region being imaged.

Thus in X-ray, for instance, early examples of contrast agents were insoluble inorganic barium salts which enhanced X-ray attenuation in the body zones into which they distributed. More recently the field of X-ray contrast agents has been dominated by soluble iodine containing compounds such as those marketed by Nycomed AS under the trade names Omnipaque® and Visipaque®.

Much recent work on X-ray contrast agents has concentrated on aminopolycarboxylic acid (APCA) chelates of heavy metal ions and, recognising that effective imaging of many body sites requires localization at the body sites in question of relatively high concentrations of the metal ions, there have been suggestions that polychelants, that is substances possessing more than one separate chelant moiety, might be used to achieve this.

Various bismuth compounds have been suggested in the prior art as X-ray absorbing agents. Other prior art documents focus on the use of metal chelates in diagnostic imaging, mainly in MRI. In addition, bismuth compounds have a long history in therapeutic medicine specially in treatment of gastrointestinal diseases such as ulcers. Although antiulcer agents such as the $H_2$-antagonists cimetidine and ranitidine, and more recently proton pump inhibitors such as omeprazole, have been developed, there is still medical use of bismuth compounds in ulcer treatment.

The most frequently used bismuth compounds as gastrointestinal drugs today are bismuth subnitrate and bismuth subsalicylate. Bismuth subnitrate or bismuth hydroxide nitrate oxide $(Bi_5O(OH)_9(NO_3)_4$ is prepared by hydrolysis of bismuth nitrate and is practically insoluble in water. It is usually used as a suspension (milk of bismuth). Bismuth subnitrate is also used topically in lotions and ointments. Bismuth subsalicylate or basic bismuth salicylate $(C_7H_5BiO_4)$ is also practically insoluble in water and is administered as a suspension or in the form of tablets. Products containing bismuth subsalicylate are used against indigestion, nausea and diarrhea. As an antidiarrheal agent it shows good activity against Salmonella with less activity versus *E. coli*.

Several bismuth compounds are known to be biologically active and have been suggested as active ingredients in various drug formulations. Organobismuth compounds can be used as antibacterial agents, for example against infections caused by highly resistant gram-negative bacteria (U.S. Pat. No. 3,466,366 of M&T Chem Inc); a protein-type bismuth complex is suggested for treatment of inflammation and infections in the gastrointestinal system in U.S. Pat. No. 4,153,685 (Schering Corp); bismuthyl prostanoate derivatives for ulcer control are suggested in BE 809388 (Aries R); phenylbismuth bis(2-pyridinethiol) 1-oxide as an antibacterial and antifungal agent is disclosed in U.S. Pat. No. 3,824,307 (Procter & Gamble Co); an antiinflammatory and antiulcer bismuth composition containing a mixture of trivalent bismuth, water-soluble protein, an organic acid anion and an alkali in ZA 8107456 (Schering Corp); bismuth subsalicylate in combination with other agents in a synergistic formulation for diarrhoea treatment in U.S. Pat. No. 4,588,589 (Richardson Vicks); treatment of non-ulcer dyspepsia associated with *Campylobacter pyloridis* infection with bismuth salts such as tripotassium dicitrato-bismuthate in WO 89/03219 (Borody T. J.); organo-bismuth compounds useful as anti-coccidium agents for poultry, and as insecticides in J63225391 (Nitto Kasei and Shionogi); pharmaceutical compositions for treatment of gastrointestinal disorders associated with *Campylobacter pylori* infections comprising a pharmaceutically acceptable bismuth compound and first and second antibiotic or antimicrobial agents in EP 439453 (Capability Services et al.); salts formed between rantidine and bismuth carboxylic acid complexes for treatment of gastrointestinal disorders in U.S. Pat. No. 5,008,256 (Glaxo); further salts formed between an $H_2$-receptor antagonist and a complex of bismuth with a carboxylic acid with activity against gastrointestinal conditions and against *Campylobate pylori* in U.S. Pat. No. 5,273,984 (Glaxo); a suspension for oral administration comprising a bismuth-containing pharmaceutical agent, benzoic acid and sorbic acid, polymer and water for use against various gastrointestinal disorders in U.S. Pat. No. 5,013,560 (Procter & Gamble); furan derivatives with bismuth carboxylic acid complexes for treatment of various gastrointestinal disorders including activity against *Heliobacter pylori* in U.S. Pat. No. 5,229,418 (Glaxo); bismuth polyacrylate complexes for treating gastrointestinal disorders like inflammatory bowel disease or *Heliobacter pylori* infections in WO 92/01457 (Evans B. K. et al.); salts of ranitidine with a bismuth carboxylate complex and alkali salt for treatment of various gastrointestinal disorders in GB 2248185 (Glaxo); use of rantidine bismuth citrate and antibiotics to inhibit *Heliobacter pylori* in EP 533281 (Glaxo); and ranitidine bismuth citrate and non-steroidal anti-inflammatory drugs for the treatment of inflammation diseases in GB 2262036 (Glaxo).

Finally, WO 95/06053 discloses certain substituted triphenyl bismuth compounds as X-ray contrast agents.

We have now found that certain covalent bismuth compounds give particularly effective contrast enhancement when used as contrast agents. These compounds also have activity against various microorganisms such as bacteria and fungi, and also can be used in the treatment of various gastrointestinal disorders.

Thus, one aspect of this invention is a diagnostic imaging contrast medium comprising a covalent non-cluster type bismuth compound, with the proviso that when the bismuth compound is a triphenyl bismuth compound it contains at least one further heavy atom, or at least one of the phenyl groups is unsubstituted in both of its ortho positions, or at least one of the phenyl groups is substituted in at least four of its ortho, meta and para positions. Such a medium may be used for contrast enhancement in diagnostic imaging, in particular X-ray, MRI, ultrasound imaging and scintigraphy.

For X-ray or ultrasound imaging it is preferred that the compounds comprise two or more heavy atoms where at least one of the heavy atoms is bismuth. For the sake of clarity, the word "heavy atom" means an atom with atomic number higher than 49.

For MRI the compounds would comprise bismuth and one or more MR active atoms. For the sake of clarity, the words "MR active atom" means an atom that directly or indirectly affects the MR signal. Typical MR active atoms include for example manganese, gadolinium, dysprosium, iron and fluorine.

The invention provides for example diagnostic imaging contrast media comprising a physiologically tolerable molecule of any of formulae I–IV,

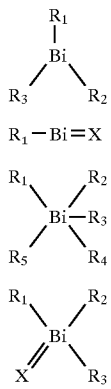

where the groups $R_1$–$R_5$ may be the same or different and are defined as any group forming a hydrolytically stable bond to bismuth. Typical $R_{1-5}$ groups are preferably aryl groups substituted with one or more heavy atoms, preferably Bi and I. X is O, S or $NR_6$ where $R_6$ is lower alkyl, for example $C_{1-4}$-alkyl, substituted lower alkyl or an aryl group.

Viewed from another aspect, the invention provides a diagnostic imaging contrast medium comprising a physiologically tolerable multinuclear bismuth complex of formula V,

where $M_mB_nA_p$ is a multinuclear entity where each M which may be the same or different is a contrast enhancing heavy metal atom and at least one M is Bi (and preferably each M is Bi) and each M is covalently bonded to at least one atom B when n is non-zero; each B which may be the same or different is a non-metal bridging atom covalently bonded to at least two M atoms and optionally to further atoms; each A which may be the same or different is a non-metal non-bridging atom covalently bonded to an M atom; each L which may be the same or different is a ligand co-ordinately bonded to at least one Bi atom; m is a positive integer of value 2 or greater; n, p and y are independently zero or positive integers provided that n and p are not simultaneously zero; x is a positive integer; or a physiologically tolerable salt thereof, together with at least one pharmaceutical excipient.

Viewed from another aspect, the invention also provides the use of bismuth compounds as defined above for the manufacture of contrast media for use in imaging of the human or non-human body.

Viewed from a still further aspect, the invention provides a method of generating an image of a human or non-human animal, preferably mammalian, body which method comprises administering to said body a physiologically tolerable contrast enhancing amount of a bismuth compound as defined above and generating an image of at least part of said body into which said agent distributes, e.g. by X-ray, MRI or ultrasound imaging or scintigraphy.

Viewed from a still further aspect the invention also provides a diagnostic imaging contrast medium comprising a bismuth compound as defined above together with at least one sterile pharmaceutical carrier or excipient.

Viewed from a still further aspect the invention also provides the use of bismuth compounds as defined above for the manufacture of therapeutic agents for treatment of infections, for example caused by *Heliobacter pylori,* and gastrointestinal disorders.

Viewed from a still further aspect, the invention provides a method of treating an infection, for example caused by *Heliobacter pylori,* or a gastrointestinal disorder of a human or non-human animal, preferably mammalian, body which method comprises administering to said body a physiologically tolerable dose of a bismuth compound as defined above.

The bismuth compounds defined above have particular potential as contrast agents since the compounds have a relative high concentration of heavy elements including bismuth. The use of these compounds enables a high ratio of contrast enhancing atom to overall structure volume to be achieved. Thus by increasing the relative content of contrast enhancing atoms in this way the total quantity of the contrast agent necessary in order to achieve the same contrast effect may be reduced and thus problems associated with contrast agent solubility or toxicity or osmolality or with contrast medium viscosity may also be reduced.

As mentioned above, it is preferred that the bismuth compounds of the invention comprise two or more contrast enhancing atoms. Both the covalent bismuth molecules and multinuclear cluster chelates also contain further atoms which may have little or no contrast enhancing effect but which may for example function as bridging atoms binding the contrast enhancing atoms together in a cluster (See WO 92/17215 for further examples of these types of structures). Other non-contrast active atoms in the contrast agent function for example as detoxification groups, as solubilizing groups, in groups for targeting of the bismuth atom and the other contrast-active atoms to the area of interest, or the non-contrast active atoms help-to stabilize the covalent molecule or chelate against hydrolysis and metabolism.

The bismuth compounds described above may, as pointed out above, be used in various modalities in medical imaging and in certain specific therapeutic fields. Some bismuth compounds are active in more than one modality. The choice of modality should be carefully taken into consideration in design of the agent. For example if the agent is intended for use in MRI, MR active elements such as fluorine and/or paramagnetic elements such as manganese or gadolinium preferably form part of the molecule.

However, one of the most interesting applications of these new bismuth containing compounds is in X-ray imaging. For use as an X-ray contrast agent, it is preferred that the compounds contain bismuth and at least one more heavy atom. The preferred bismuth compounds may in addition to bismuth contain atoms such as iodine, lanthanides, transition metals, or other metal atoms. Examples include Gd, Ce, Sr, Y, Zr, Ru, Rh, In, Ta, Nb, Dy, Hf, W, I/ Mo, Re, Os, Pb, Ba, Ga, Sn, Hg and Tl. Bismuth compounds containing several bismuth and/or several iodine atoms are most preferred. The choice of heavy atom and the number of heavy atoms in each unit are determined by a variety of factors including the toxicity of the overall molecule or cluster complex, the in vitro and in vivo (shelf life) stability of the unit and the X-ray absorption characteristics of the heavy atom. In this regard it should be noted that while the X-ray absorbtion cross section for atoms generally increases with increasing atomic number, the absorption cross section is itself dependent on the X-ray wavelength and increases with increasing photon energy until slighthly above a value termed the K-edge whereafter attenuation decreases. Thus there are photon energy ranges for which one element is a better X-ray attenuator than a second even though outside these ranges the second element may be the better attenuator. Consequently the bismuth compounds according to the invention will each have optimum photon energy ranges making them particularly suitable for operation with X-ray imaging apparatus utilizing X-rays having such photon energy ranges. However, by choosing bismuth compounds containing atoms of more than one heavy element one may create X-ray contrast agents having optimal performance in more than one photon energy band or over a broader band. The compounds used according to the present invention are thus particularly attractive since they can be selected so as to match their X-ray attenuation profiles with the X-ray emission profiles of particular X-ray sources—in effect the invention provides "tunable" X-ray contrast media. From an efficacy point of view, bismuth and uranium are the heavy atoms with the highest efficacy per atom in all X-ray modalities (CT, plain X-ray and DSA).

In formula I–IV above, $R_1$–$R_5$ may be the same or different and may be any group forming a hydrolytically stable bond to bismuth. Typical $R_1$–$R_5$ groups can for example be aryl groups, optionally substituted with one or more heavy atoms such as Bi and I. For extracellular X-ray contrast agents the $R_{1-5}$ groups are usually substituted with one or more (preferably more) hydrophilic groups. Such compounds should in general have a low charge or preferably no charge.

The bond from bismuth to one of the $R_{1-5}$ groups may for example be of the following types: Bi—C, Bi—O, Bi—S and Bi—N. Some of these bonds are more stable than others and it is known in the literature on the chemistry of bismuth that the stability of the bismuth molecule is very dependent on the chemical nature of this bond and the substituents (see for example Chapter 28 in G. Wilkinson (ed) Comprehensive Coordination Chemistry; Gmelin Handbuch der Anorganischen Chemie Volume 47; L. D. Freedman and G. O. Doak in Chem. Rev (1982) 82 15–57; Methoden der Organischen Chemie (Houben-Weyl) Volume XIII/8; Comprehensive Organometallic Chemistry, Chapter 13; Kirk-Othmer: Encyclopedia of Chemical Technology Volume 3 p 921–936).

Some trialkylbismuth compounds are known to be very hydrolytically unstable, however, we have shown that triarylbismuth compounds are surprisingly stable against hydrolysis: triphenylbismuth dissolved in aqueous (25%) tetrahydrofuran is stable under reflux for many days. When the $R_{1-5}$-groups form Bi—C bonds, aryl groups are generally preferred. At least one of the $R_{1-5}$-groups should be an aryl group or substituted aryl group. The term "aryl group" here means any aromatic hydrocarbon ring system or aromatic heterocyclic system. Typical ring systems include for example benzene, naphthalene, indene, fluorene, phenalene, phenanthrene, anthracene, fluoranthene, acephenanthrylene, aceanthrylene, triphenylene, pyrene, chrysene, naphthacene, pleiadene, picene, perylene, pentaphene, pentacene, tetraphenylene, hexaphene, hexacene, rubicene, coronene, trinaphthylene, heptaphene, rubicene, coronene, heptacene, pyranthrene, ovalene, furan, thiophene, thianthrene, pyran, isobenzofuran, chromene, xanthene, phenoxathin, pyrrole, imidazole, pyrazole, isothiazole, isoxazole, pyridine, pyrazine, pyrimidine, pyradizine, indolizine, isoindole, indole, indazole, purine, quinolizine, isoquinoline, quinoline, phtalazine, naphyhyridine, quinoxaline, quinazoline, cinnoline, pteridine, carbazole, β-carboline, phenanthridine, acridine, permidine, phenanthroline, phenazine, phenarsazine, phenothiazine, furazan, phenoxazine, isochroman, chroman, indoline and isoindoline.

Possible alkyl groups include both substituted or unsubstituted lower and higher alkyl, alkoxy, polyalkoxy and alkylaryl groups, or any other groups.

The $R_{1-5}$ groups may be substituted with contrast active elements or contrast active groups and other non-contrast active elements or groups. Typical contrast active elements are listed above. The most preferred contrast active elements for X-ray imaging are iodine and bismuth. Other substituents include fluorine, chlorine, bromine, alkyl, alkoxy, substituted alkyl for example hydroxyalkyl or polyhydroxyalkyl, substituted alkoxy for example hydroxyalkoxy or polyhydroxyaloxy, amides including substituted amides such as —$NAcR_6$ and —$CONR_7R_8$ where Ac is an acyl group and $R_6$–$R_8$ which may be the same or different represent lower alkyl, $C_{1-4}$-hydroxyalkyl, carboxy- or amino-$C_{1-4}$-alkyl groups or together both $R_7$ and $R_8$ represent a cyclic group such as —$CH_2CH_2NR_9CH_2CH_2$— where $R_9$ for example is a $C_{1-4}$ alkyl group optionally substituted by hydroxyl, carbonyl, aryl or amino groups.

Particularly conveniently, the multinuclear bismuth complexes are presented as their chelate complexes containing EDTA or other APCAs. Such chelate complexes are remarkably stable with regard to release of the heavy metal ions. It is particularly preferred that the electrical charge carried by the complexing moieties should substantially if not completely balance that carried by the complexed entity; for APCA chelants this may easily be achieved for example by omission, replacement or deactivation (e.g. by ester or amide formation) of one or more of the carboxyl moieties.

Many suitable chelants are widely known or have been described in the literature, especially literature relating to heavy metal detoxification agents, bifunctional chelants and chelate-based contrast agents, e.g. those described in WO-A-89/00557 (Berg) and the documents mentioned therein and in the search report appended thereto, U.S. Pat. No. 4,647,447 (Gries), U.S. Pat. No. 4,826,673 (Dean), EP-A-230893 (Felder), EP-A-217577 (Frincke), U.S. Pat. No. 4,652,519 (Warshawsky), U.S. Pat. No. 4,687,659 (Quay), and numerous other recent patent publications of Nycomed AS, Salutar Inc, Schering AG, Squibb, Bracco, Mallinckrodt, Dow and Guerbet.

While polyamines, especially linear or cyclic polyamines, such as ethylenediamine, 1,4,7-triazacyclononane and cyclen, can be used as chelants, in general APCAs are preferred, particularly DTPA, EDTA and derivatives thereof and other cyclic and non-cyclic APCAs as defined in WO-A-89/00557.

Examples of suitable chelants include compounds of formulae:

$(HOOCCH_2)_2NCH_2CH_2N(CH_2COOH)_2$ (i)

$(HSCH_2CH_2)_2NCH_2CH_2N(CH_2CH_2SH)_2$ (ii)

$H_2NCH_2CH_2N(CH_2COOH)CH_2CH_2N(CH_2COOH)CH_2CH_2NH_2$ (iii)

$H_2NCH_2CH_2N(CH_2CH_2SH)CH_2CH_2N(CH_2CH_2SH)CH_2CH_2NH_2$ (iv)

$HOOCCH_2(NCH_2CH_2)_3NCH_2COOH$ (v)

$HSCH_2CH_2(NCH_2CH_2)_4SH$ (vi)

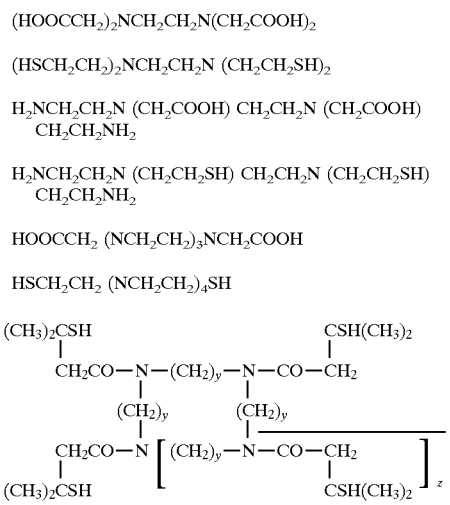 (vii)

(where y=6,7,8,9 or 10 and z=0 or 1)

$(HOOCCH_2)_2NH$ (viii)

$(HSCH_2CH_2)_2NH$ (ix)

$(HOOCCH_2)_2NCH_2CH_2N(CH_2COOH)CH_2CH_2N(CH_2COOH)CH_2CH_2N(CH_2COOH)_2$ (x)

$(HSCH_2CH_2)_2NCH_2CH_2N(CH_2CH_2SH)CH_2CH_2N(CH_2CH_2SH)CH_2CH_2N(CH_2CH_2SH)_2$ (xi)

$(HOOCCH_2)_2N(CH_2CH_2NH)_2CH_2CH_2N(CH_2COOH)_2$ (xii)

$(HSCH_2CH_2)_2N(CH_2CH_2NH)_2CH_2CH_2N(CH_2CH_2SH)_2$ (xiii)

pyridine-2,6-dicarboxylic acid (xiv)

2,6-bis-merceptomethyl-pyridine (xv)

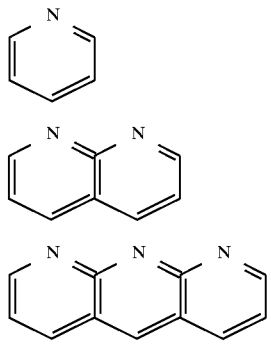

(xvi)

(xvii)

(xviii)

tetra-N-alkyl-ethylenediamine (xix)

penta-N-alkyl-diethylenetriamine (xx)

and the phosphorus analogues of these nitrogen-donor based ligands.

Chelants such as NTA, IDA, EDTA, HEDTA, DTPA, DTPA-BMA, HEDDA, TTDA, EDTA-BMA, TBEDDA, MEEDDA, TTHA, EDDA, EHPG, PDTA, CHDTA, HPDTA and triazacyclononane monoacetic acid, especially PDTA and EDTA, are of particular interest.

Particularly preferred chelants include cyclen, EDTA, DTPA, DOTA, DO3A, HP-DO3A, the 6-oxa and 6-thia analogues of DTPA and amides thereof, e.g. DTPA-BMA and DTPA-BMO (6-carboxymethyl-3,9-bis(morpholinocarbonylmethyl)-3,6,9-triazaundecanedioic acid—the Gd(III) chelate of which is sometimes referred to as gadopenamide).

Where the chelant is to be attached to a macromolecule, this may conveniently be any tissue, organ or cell targeting macromolecule, for example a biomolecule such as a protein, an antibody or antibody fragment, or alternatively it may be a biologically relatively inert material such as a polysaccharide or poly-sugar alcohol, e.g. dextran or starch. Such macromolecules are discussed extensively in the recent literature relating to contrast agents.

The bismuth compounds used according to the invention may be ionic or, more preferably, may carry no net charge; most preferably the compound is non-ionic. Moreover they may be water-soluble or, less preferably, water-insoluble. Compounds with low solubility in water could be used as X-ray contrast agents for liver, spleen, lymphatic blood pool and gastrointestinal system imaging. Water-soluble macromoleculaɪ bismuth compounds (mw>20000) could be used as blood pool X-ray contrast agents. Any necessary counterions should of course most preferably also be physiologically tolerable.

The range of physiologically acceptable counterions for therapeutically active bismuth agents is of course well known to pharmacologists.

Suitable counter-ions include for example protons, alkali and alkaline earth metal ions, e.g. sodium, calcium and magnesium and zinc, ammonium and organic cations (e.g. organic amine cations, iodinated organic amine cations, quarternary ammonium, pyridinium, meglumine, alkylammonium, polyhydroxy-alkylammonium, basic protonated amino acids etc.), transition metal complex cations and organometallic cations.

Suitable counter-ions also include for example halide (e.g. choride, bromide, iodide and $I_3^-$).

The invention also provides novel covalent non-cluster type bismuth compounds, with the proviso that when the bismuth compound is a triphenyl bismuth compound it contains at least one further heavy atom, or at least one of the phenyl groups is substituted in at least four of its ortho, meta and para positions and the molecule as a whole contains at least one hydroxy group. Preferably the compounds also contain at least one further covalently bonded bismuth atom or at least one covalently bonded iodine atom.

This invention thus provides new bismuth compounds of formula I which may be represented as follows:

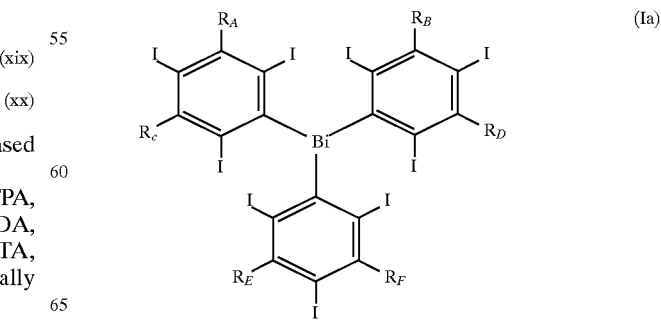

(Ia)

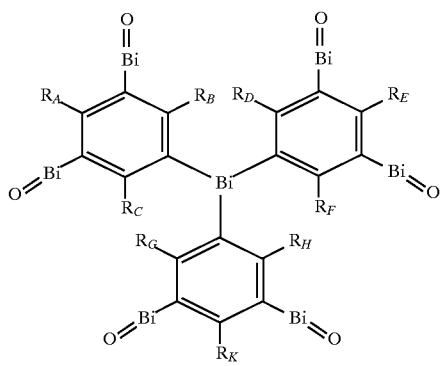
(Ib)

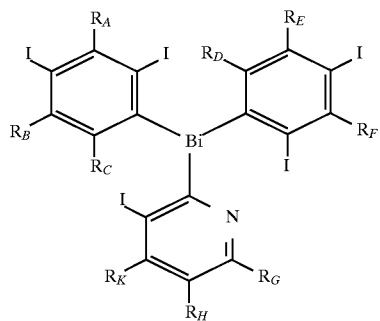
(Ic)

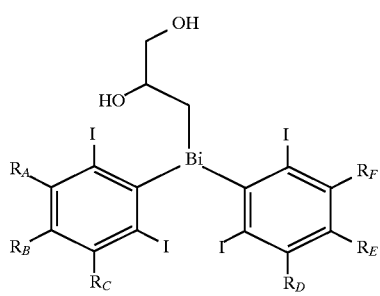
(Id)

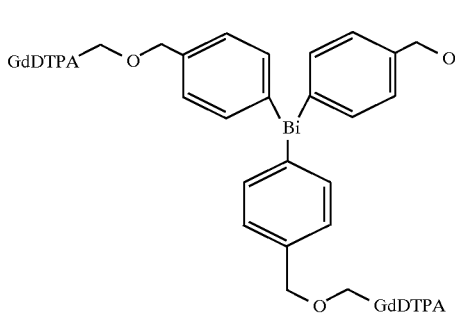
(Ie)

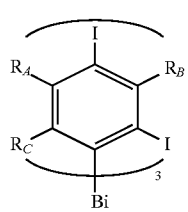
(If)

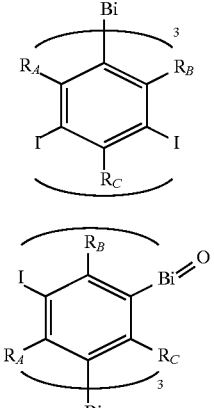
(Ig)
(Ih)

$R_{A-K}$ in formulae (Ia)–(Ih) can be the same or different. Typical $R_{A-K}$ groups can for example be —COOH, —NHCOCH$_3$, —N(Me)COCH$_3$, —CONHCH$_3$, —CONHCH$_2$CH$_2$OH, —CONHCH$_2$CONHCH$_3$, —NHCOCHOHCH$_3$, —NHCOCH$_2$OCH$_3$, —CONHCH$_2$CHOHCH$_2$OH, —CON(Me)CH$_2$CHOHCH$_2$OH, —CONHCH(CH$_2$CH$_2$OH)$_2$, —CONHCH(CH$_2$OH)$_2$ CHOHCH$_2$OH, —CONHCH(CH$_2$OH).CHOH.CHOH.CH$_2$OH, —OCH$_2$CH$_2$OH, —NHCOCH$_2$OH, —CH$_2$OH and N (COCH$_2$OH) (CH$_2$CH$_2$OH).

This invention also provides new bismuth compounds of formula II which may be represented as follows:

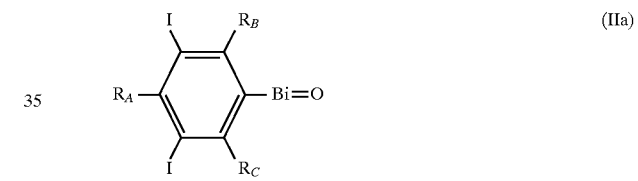
(IIa)

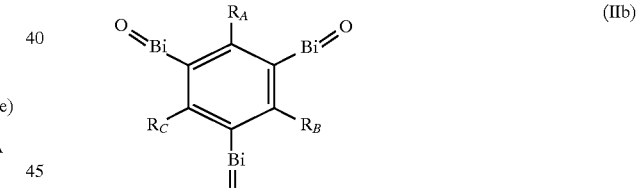
(IIb)

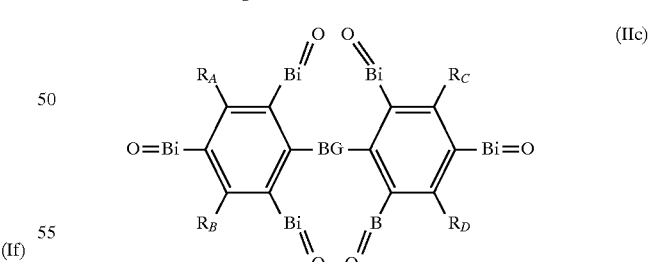
(IIc)

$R_A$–$R_D$ in formulae (IIa)–(IIc) can be the same or different and typical $R_{A-D}$ groups are listed above. BG can be any bridging group. In the compounds of the invention, the linker group BG is conveniently a 1, 2 or 3 membered chain comprising carbon, nitrogen, oxygen or sulphur atoms, e.g. a O, S, N or C one atom chain, a NN, NC, NS, CC or CO two atom chain, or a NCN, OCN, CNC, OCO, NSN, CSN, COC, OCC or CCC three atom chain, for example: an oxygen atom or a group $NR^1$, $CO$, $SO_2$ or $CR_2^1$; a group $COCO$, $CONR^1$, $COCR_2^1$, $SOCR_2^1$, $SO_2NR^1$, $CR_2^1CR_2^1$, $CR_2^1NR^1$ or $CR_2^1O$; a group $NR^1CONR^1$, $OCONR^1$, $CONR^1CO$, $CONR^1CR_2^1$, $OCOO$, $CR_2^1OCR_2^1$, $OCR_2^1CO$, $CR_2^1CONR^1$, $CR_2^1CR_2^1CR_2^1$, $COCR^1R^1CO$, $CR_2^1NR^1CR_2^1$, $CR_2^1SO_2NR^1$, $CR_2^1OCO$, or $NR^1SO_2NR^1$; where $R^1$ is hydrogen or a $C_{1-6}$-alkyl or alkoxy group optionally substituted by hydroxy, alkoxy, oxa or oxo (e.g. a polyhydroxyalkyl, formyl, acetyl, hydroxyl, alkoxy or hydroxyalkoxy group), or where attached to a carbon $R^1$ may also be a hydroxyl group.

Advantageously, the BG group is not symmetrical. This may be achieved for example by asymmetrical substitution of a symmetrical chain (e.g. N—C—N substituted as $NHCONR^1$) or by selection of an asymmetric chain (e.g. OCN substituted as $OCONR^1$). In particular, it is preferred that the linker group BG should be polar and also that it should be hydrophilic.

Other examples of bridging groups include —NHCO$(CH_2)_n$ CONH—, —NHCO—$(CH_2OCH_2)_n$—CONH—, —NHCOCH$_2$(CH$_2$OCH$_2$)$_n$CH$_2$CONH—, —CONHCH$_2$—(CHOH)$_n$CH$_2$NHCO—, —NH(Ac)CH$_2$(CHOH)$_n$CH$_2$N(Ac)— and —NHCOCH$_2$CH$_2$SCH$_2$CH$_2$CONH— where n is an integer between 1 and 6.

This invention further provides new bismuth compounds of formula III which may be represented as follows:

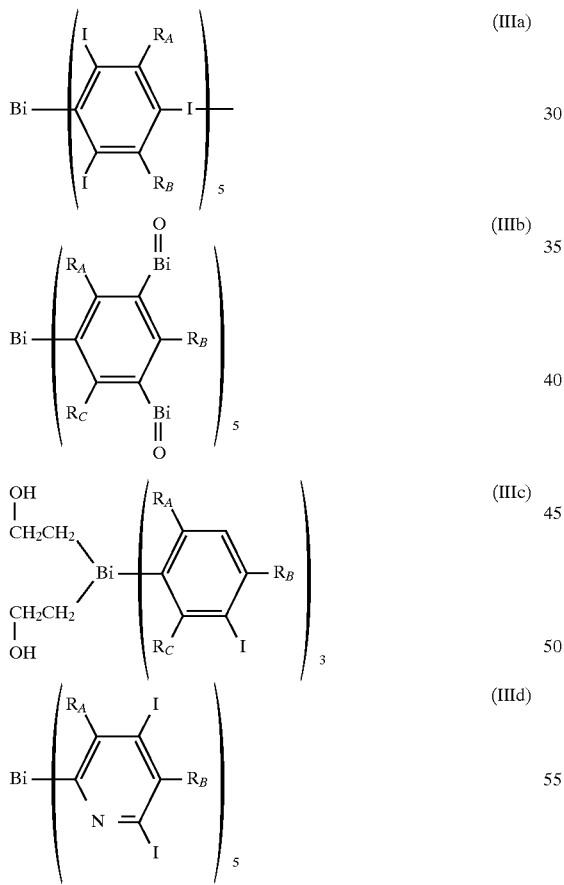

The $R_A$–$R_C$ groups in each of the molecules (for example in IIIa) may be the same or different and typical $R_A$–$R_C$ groups are described above.

This invention also provides new bismuth compounds of formula IV which may be represented as follows:

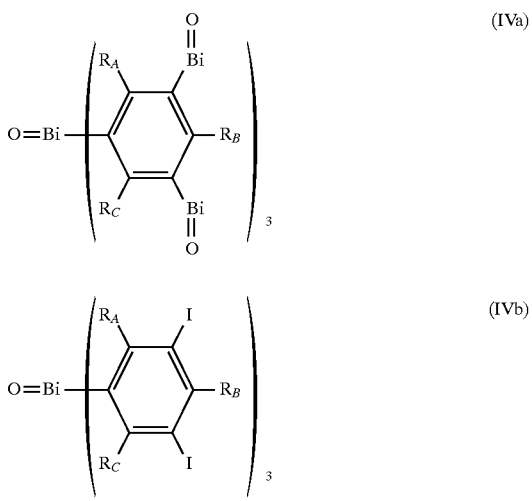

The $R_A$–$R_C$ groups in each of the above molecules (for example in IVa) may be the same or different and typical $R_A$–$R_C$ groups are described above.

Bismuth compounds of formula V can be represented for example by the following cores:

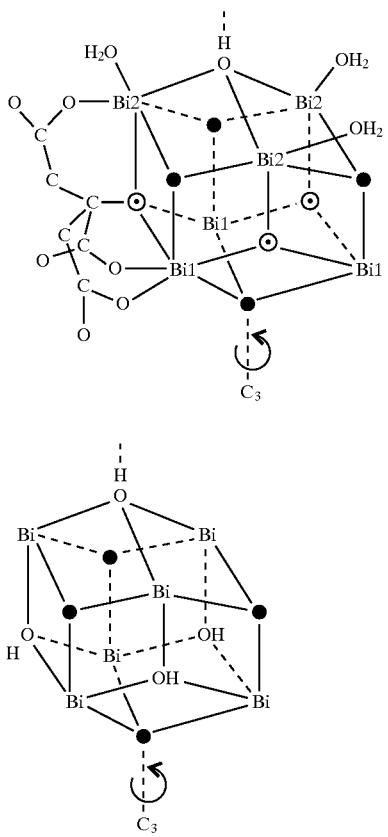

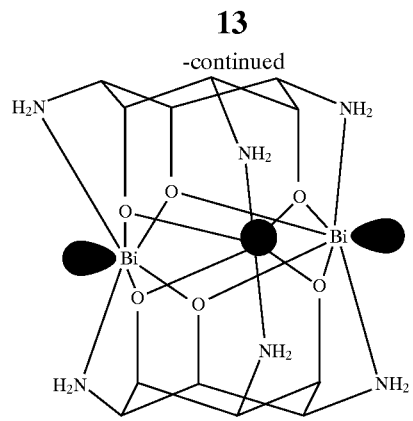

The bismuth compounds can be prepared from cheap and easily available bismuth salts. The general synthesis of covalent bismuth compounds is well described in the above cited reviews on bismuth chemistry.

Thus for example, bismuth compounds of formula I can be synthesized from bismuth (III) chloride as follows:

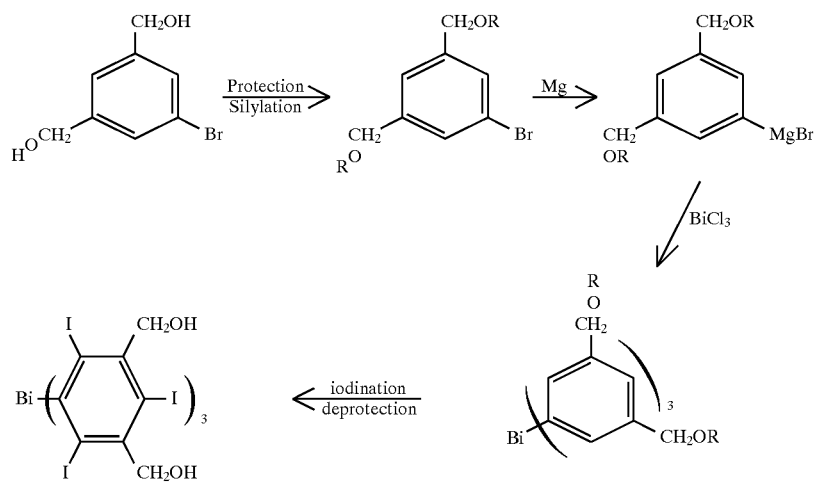

Bismuth compounds of formula II may for example be synthesized from triiodinated X-ray contrast agent derivatives and bismuthoxychloride as follows:

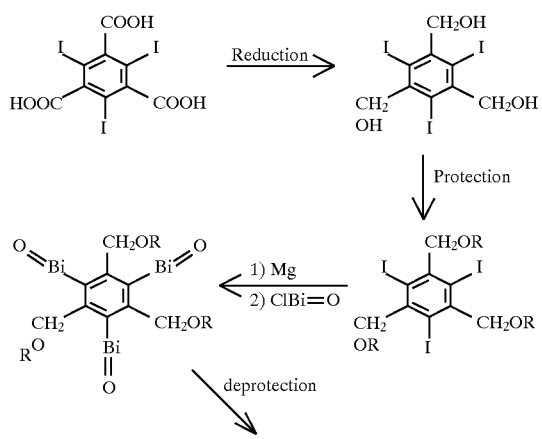

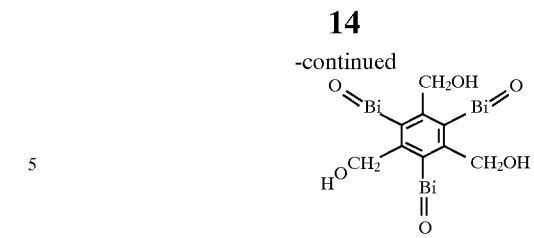

Bismuth compounds of formula III (with bismuth oxidation number 5) may be prepared by halogenation of bismuth compounds of formula I followed by a Grignard reaction or using another organometallic reagent such as the lithium salt as illustrated below:

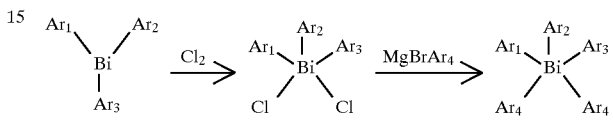

Bismuth compounds of formula IV may be prepared from the dichlorides as follows:

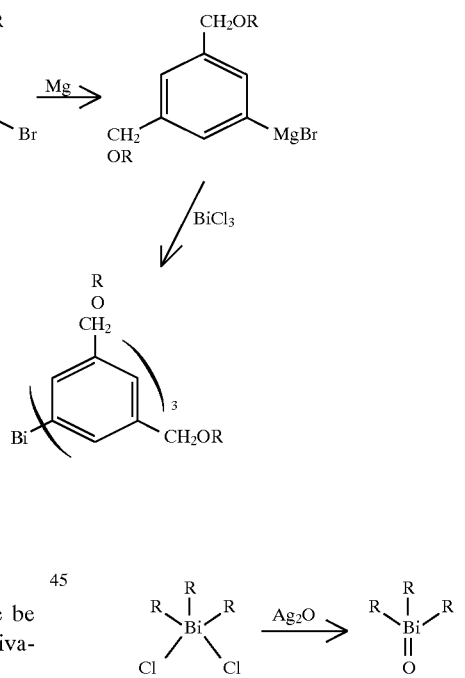

For administration to human or animal subjects, the bismuth compounds will conveniently be formulated together with pharmaceutical or veterinary carriers or excipient. The contrast media of the invention may conveniently contain pharmaceutical or veterinary formulation aids, for example stabilizers, antioxidants, osmolality adjusting agents, buffers, pH adjusting agents, colorants, flavours, viscosity adjusting agents and the like. They may be in forms suitable for parenteral or enteral administration, for example, injection or infusion or administration directly into a body cavity having an external voidance duct, for example the gastrointestinal tract, the bladder and the uterus. Thus the media of the invention may be presented in conventional pharmaceutical administration forms such as tablets, coated tablets, capsules, powders, solutions and suspensions although dispersions in physiologically acceptable carrier media, e.g. water for injections, will generally be preferred. Where the medium is formulated for parenteral administration, the carrier medium incorporating the bismuth compound is preferably isotonic or somewhat hypertonic. Moreover, media for parenteral administration may contain small quantities, e.g. 0.01 to 10 mole percent relative to the bismuth compound, of free chelants or weak chelate complexes with physiologically tolerable chelated species (e.g. $Ca^{2+}$); small additions of sodium or calcium salts may also advantageously be made.

For use in X-ray imaging the media of the invention should generally have a heavy atom content of 1 millimole/l to 5 mole/l, preferably 0.1 to 2 mole/l. Dosages of from 0.05 to 2.0 mmoles/kg, e.g. 0.5 to 1.5 mmoles/kg, will generally be sufficient to provide adequate contrast although dosages of 0.8 to 1.2 mmoles/kg will normally be preferred.

For scintigraphy, dosages of the radioactive species will generally be significantly lower.

Polymers with the bismuth compounds incorporated, for example bound to the polymer molecules, may be used in medical catheters.

Thus in summary the present invention provides a particularly effective means by which contrast media efficiency may be enhanced by increasing the relative proportion of molecular volume that is occupied by the contrast enhancing heavy or paramagnetic metal atom. For X-ray contrast media in particular, this also enables higher K-edge value atoms than the iodine of the now conventional X-ray contrast media to be utilized effectively.

The present invention will now be illustrated further by the following non-limiting Examples (all ratios and percentages are by weight and all temperatures are in degrees Celsius unless otherwise specified):

EXAMPLE 1

Triphenylbismuth Suspension

Human serum albumin (HSA) (3 g) is dissolved in distilled water (150 ml). The solution is filtered through a membrane filter with pore size 0.45 micron. A filtered solution (0.22 micron) of triphenylbismuth (Fluka) (1.0 g) in 96% ethanol (25.0 ml) is slowly added to the HSA solution under vigorous stirring over a prolonged period of time. The microparticles formed are centrifuged and are washed repeatedly. The particles are dispersed in a sterile filtered isotonic 0.9% sodium chloride/water for injection solution (100 ml) under vigorous stirring until a homogeneous suspension is achieved.

EXAMPLE 2

Freeze Dried Powder Comprising Tris(4-Carboxyphenyl)Bismuth Trisodium Salt For Dissolution In Water Prior To Injection Tris(4-carboxyphenyl)bismuth is prepared according to Supniewski, J. in Rocniki Chem 6 (1926) 97, and the compound (5.0 g) is dissolved in water by addition of three equivalents of sodium hydroxide. The solution is filled into a 50 ml vial and freeze dried.

EXAMPLE 3

Dodecafluorodibismatriptycene ($C_{18}Bi_2F_{12}$) Suspension For Blood Pool And Liver X-ray And MRI Diagnosis Dodecafluorodibismatriptycene is prepared according to Cullen, W. R et al in J. Fluorine Chem 8 (1976) 183. A solution containing 0.4% HSA and 2% propylene glycol in distilled water is prepared (60.0 ml) and filtered through a membrane filter (0.45 micron).

A filtered solution of dodecafluorodibismatriptycene (0.6 g) in tetrahydrofuran (20.0 ml) is slowly added to the aqueous HSA/propylene glycol solution under vigorous homogenizing.

The microparticles formed are centrifuged and are washed repeatedly before the particles are dispersed in a sterile solution of 0.05% polysorbate 80 in saline (5.3 ml).

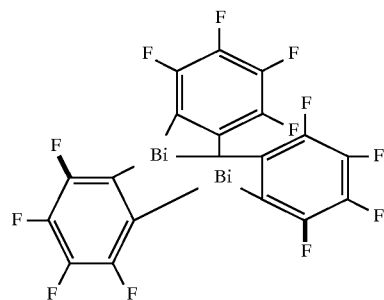

(stable compound containing 2 bismuth atoms.)

We claim:

1. A composition comprising a covalent non-cluster type bismuth compound for diagnostic imaging and a sterile pharmaceutical carrier or excipient.

2. A composition medium as claimed in claim 1 wherein the bismuth compound contains at least one other heavy atom.

3. A composition medium as claimed in claim 1 wherein the at least one other atom is selected from iodine, bismuth, lanthanides, transition metals and other metal atoms.

4. A diagnostic imaging contrast medium comprising a physiologically tolerable molecule selected from formulae I–IV,

  (I)

  (II)

  (III)

  (IV)

where the groups $R_1$–$R_5$ may be the same or different and are groups forming a hydrolytically stable bond to bismuth and X is O, S or $NR_6$ where $R_6$ is lower alkyl, substituted lower alkyl or an aryl group, together with a sterile pharmaceutical carrier or excipient.

5. A diagnostic imaging contrast medium as in claim 4 wherein R1–R5 are selected from aryl groups substituted with one or more heavy atoms and X is O, S or NR6 where R6 is lower alkyl, substituted lower alkyl or an aryl group.

6. Bismuth compounds of formulae

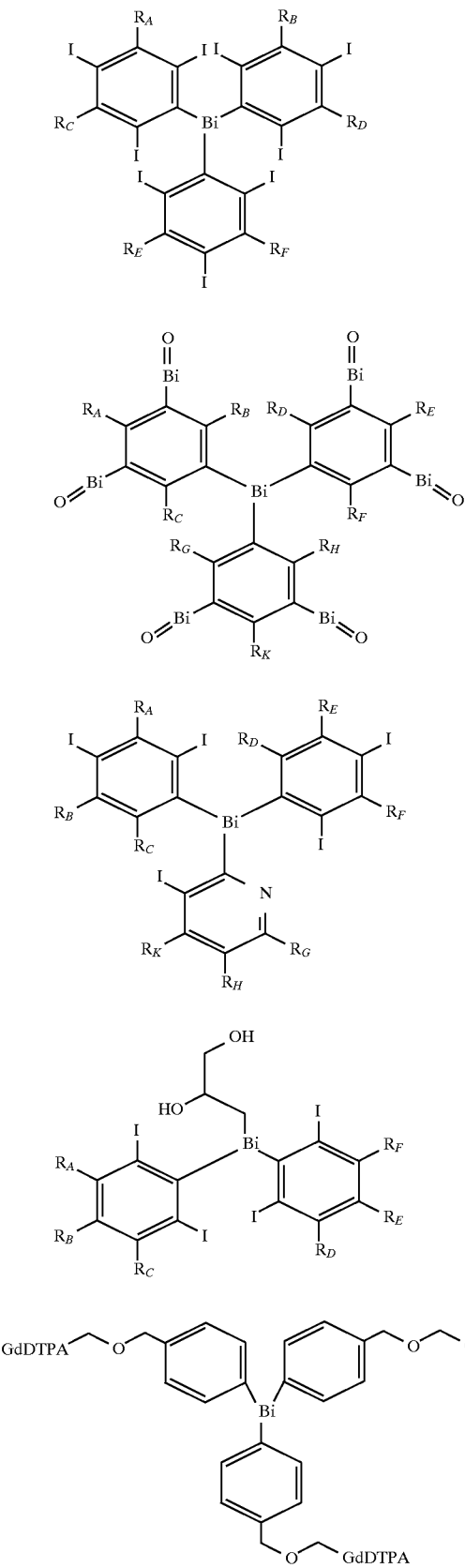

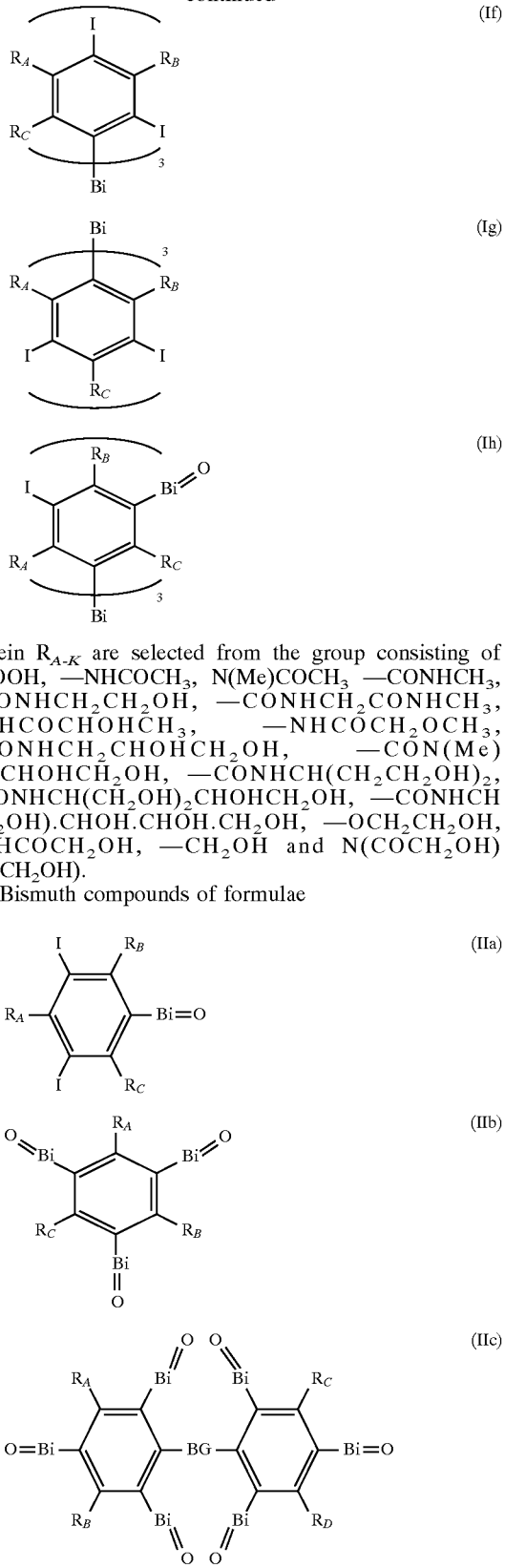

wherein $R_{A-K}$ are selected from the group consisting of —COOH, —NHCOCH$_3$, N(Me)COCH$_3$ —CONHCH$_3$, —CONHCH$_2$CH$_2$OH, —CONHCH$_2$CONHCH$_3$, —NHCOCHOHCH$_3$, —NHCOCH$_2$OCH$_3$, —CONHCH$_2$CHOHCH$_2$OH, —CON(Me)CH$_2$CHOHCH$_2$OH, —CONHCH(CH$_2$CH$_2$OH)$_2$, —CONHCH(CH$_2$OH)$_2$CHOHCH$_2$OH, —CONHCH(CH$_2$OH).CHOH.CHOH.CH$_2$OH, —OCH$_2$CH$_2$OH, —NHCOCH$_2$OH, —CH$_2$OH and N(COCH$_2$OH)(CH$_2$CH$_2$OH).

7. Bismuth compounds of formulae wherein $R_{A-D}$ is selected from the group consisting of —COOH, —NHCOCH$_3$, —N(Me)COCH$_3$, —CONHCH$_3$, —CONHCH$_2$CH$_2$OH, —CONHCH$_2$CONHCH$_3$, —NHCOCHOHCH$_3$, —NHCOCH$_2$OCH$_3$, —CONHCH₂CHOHCH₂OH, —CON(Me)CH₂CHOHCH₂OH, —CONHCH(CH₂CH₂OH)₂, —CONHCH(CH₂OH)₂CHOHCH₂OH, —CONHCH(CH₂OH).CHOH.CHOH.CH₂OH, —OCH₂CH₂OH, —NHCOCH₂OH, —CH₂OH, and N(COCH₂OH)(CH₂CH₂OH) and BG is a bridging group.

8. Bismuth compounds of formulae (IIc) as claimed in claim 7 wherein BG is a 1, 2 or 3 membered chain comprising carbon, nitrogen, oxygen or sulphur atoms, selected from the group consisting of a O, S, N or C one atom chain, a NN, NC, NS, CC or CO two atom chain, or a NCN, OCN, CNC, OCO, NSN, CSN, COC, OCC or CCC three atom chain.

9. Bismuth compounds as in claim 8 wherein BG is an oxygen atom or a group NR¹, CO, SO₂ or CR¹₂; a group COCO, CONR¹, COCR¹₂, SOCR¹₂, SO₂NR¹, CR¹₂CR¹₂, CR¹₂NR¹ or CR¹₂O; a group NR¹CONR¹, OCONR¹, CONR¹CO, CONR¹CR¹₂, OCOO, CR¹₂OCR¹₂, OCR¹₂CO, CR¹₂CONR¹, CR¹₂CR¹₂CR¹₂, COCR¹NR¹CO, CR¹₂NR¹CR¹₂, CR¹₂SO₂NR¹, CR¹₂OCO, or NR¹SO₂NR¹; where R¹ is hydrogen or a C₁₋₆ alkyl or alkoxy group optionally substituted by hydroxy, alkoxy, oxa or oxo or, where attached to a carbon, R¹ may also be a hydroxyl group.

10. Bismuth compounds of formulae

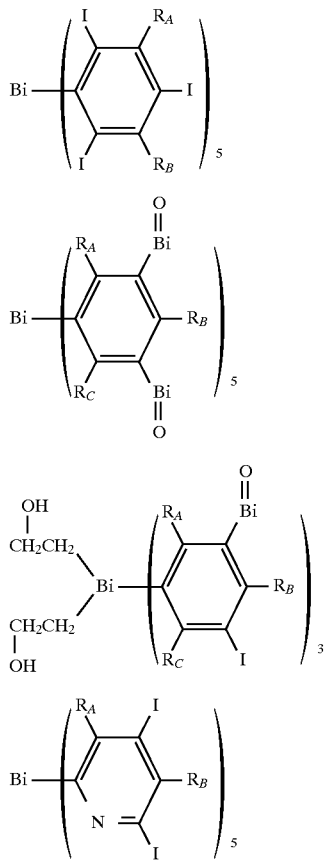

(IIIa)

(IIIb)

(IIIc)

(IIId)

wherein $R_{A-C}$ are selected from the group consisting of —COOH, —NHCOCH₃, —N(Me)COCH₃, —CONHCH₃, —CONHCH₂CH₂OH, —CONCH₂CONHCH₃, —NHCOCHOHCH₃, —NHCOCH₂OCH₃, —CONHCH₂CHOHCH₂OH, —CON(Me)CH₂CHOHCH₂OH, —CONHCH(CH₂CH₂OH)₂, —CONHCH(CH₂OH)₂CHOHCH₂OH, —CONHCH(CH₂OH).CHOH.CHOH.CH₂OH, —OCH₂CH₂OH, —NHCOCH₂OH, —CH₂OH and N(COCH₂OH)(CH₂CH₂OH).

11. Bismuth compounds of formulae

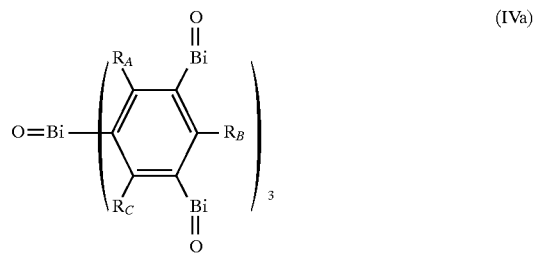

(IVa)

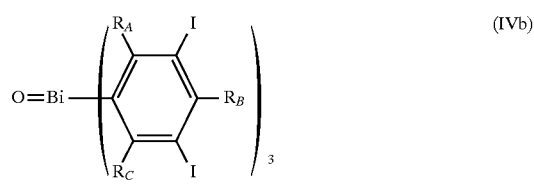

(IVb)

wherein $R_{A-C}$ are selected from the group consisting of —COOH, —NHCOCH₃, —N(Me)COCH₃, —CONHCH₃, —CONHCH₂CH₂OH, —CONHCH₂CONHCH₃, —NHCOCHOHCH₃, —NHCOCH₂OCH₃, —CONHCH₂CHOHCH₂OH, —CON(Me)CH₂CHOHCH₂OH, —CONHCH(CH₂CH₂OH)₂, —CONHCH(CH₂OH)₂CHOHCCH₂OH, —CONHCH(CH₂OH).CHOH.CHOH.CH₂OH, —OCH₂CH₂OH, —NHCOCH₂OH, —CH₂OH and N(COCH₂OH)(CH₂CH₂OH).

12. A covalent, non-cluster bismuth compound which contains at least one additional heavy atom.

13. The bismuth compound according to claim 12 containing at least one additional covalently bonded bismuth atom.

14. The bismuth compound according to claim 12 containing at least one covalently bonded iodine atom.

* * * * *